United States Patent [19]
Hay

[11] 4,127,605
[45] Nov. 28, 1978

[54] SUBSTITUTED CARBAMATE INTERMEDIATE

[75] Inventor: James V. Hay, Newark, Del.

[73] Assignee: E. I. Du Pont de Nemours and Company, Wilmington, Del.

[21] Appl. No.: 899,299

[22] Filed: Apr. 24, 1978

[51] Int. Cl.² ........................................... C07C 125/03
[52] U.S. Cl. ................................................. 260/544 C
[58] Field of Search ..................................... 260/544 C

[56] References Cited

FOREIGN PATENT DOCUMENTS 1,297,095  6/1969  Fed. Rep. of Germany ........... 260/544
2,654,282  6/1977  Fed. Rep. of Germany ........... 260/544
2,654,313  8/1977  Fed. Rep. of Germany ........... 260/544

Primary Examiner—Gerald A. Schwartz

[57] ABSTRACT

N,N'-[1,2-Ethanediylbis(thio)]bis[N-methylcarbamic fluoride] useful as an intermediate in preparation of insecticides.

1 Claim, No Drawings

SUBSTITUTED CARBAMATE INTERMEDIATE

BACKGROUND OF THE INVENTION

This invention pertains to a biscarbamyl fluoride which is useful as an intermediate for the preparation of agricultural chemicals.

Carbamoyl fluorides are known in the prior art, e.g., (a) German DT No. 2,654,313 which includes disclosures to compounds of the formula

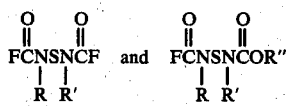

(b) German DT No. 2,654,282 which includes disclosures to compounds of the formula

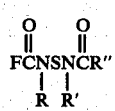

(c) German DT No. 1,297,095 which includes a disclosure to a compound of the formula

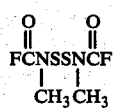

In the above patents the various R substituents are widely defined.

SUMMARY OF THE INVENTION

This invention relates to the novel compound of formula I and to a method for its preparation.

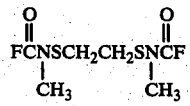

This compound is an intermediate which is particularly useful in preparing compounds which are insecticides. Two examples of such insecticides are of the formula IIa and IIb.

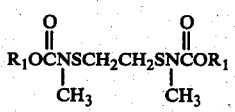

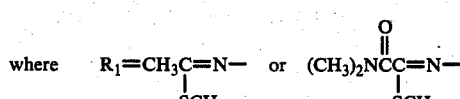

Compound IIa is disclosed in Ser. No. 812,316, filed July 1, 1977, now abandoned, and compound IIb is disclosed in Ser. No. 899,298 (BA-8256) filed concurrently with the present application.

DETAILED DESCRIPTION OF THE INVENTION

Preparation

The compound of Formula I is prepared, as shown in Equation A, by reacting two moles of N-methyl carbamyl fluoride with one mole of ethane-1,2-disulfenyl chloride in the presence of base:

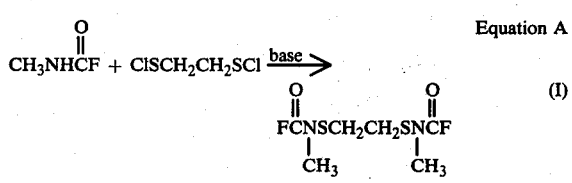

The reaction can be carried out in an inert organic solvent, e.g. benzene, toluene, the xylenes, tetrahydrofuran, dioxane, methylene chloride, chloroform, or 1,2-dichloroethane. Mixtures of these solvents may be used.

Organic or inorganic bases which can function as an acid acceptor can be used, e.g. trialkylamines such as triethylamine and trimethylamine, pyridine, N,N-dimethyl aniline, the hydroxides, carbonates, and bicarbonates of the alkali metals and alkaline earths.

The reaction shown in Equation A can be carried out at a temperature between about $-30°$ C. and $0°$ C., preferably between about $-25°$ C. and $-15°$ C. Pressure is not critical, for convenience, atmospheric pressure is preferred.

Ethane-1,2-disulfenyl chloride can be prepared by the methods described in either *Journal of Heterocyclic Chemistry*, 6, 629 (1969), or U.S. Pat. Nos. 3,855,240; 3,826,051; 3,869,435; and 3,974,163.

The synthesis of N-methyl carbamyl fluoride is taught in Belgian Pat. Nos. 843,415 and 843,416.

The compounds of Formula II can be prepared as shown in Equation B, by reacting two moles of an oxime of Formula III with one mole of the biscarbamyl fluoride of Formula I in the presence of base:

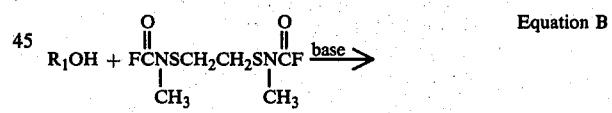

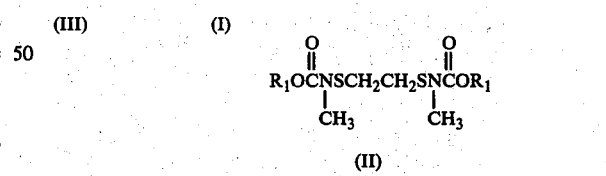

wherein $R_1$ is as previously defined.

The reaction can be carried out in an organic solvent, e.g. benzene, toluene, the xylenes, tetrahydrofuran, dioxane, methylene chloride, chloroform, 1,2-dichloroethane, or the lower alcohols, such as methanol and ethanol. Mixtures of these solvents may be used.

Organic or inorganic bases which can act as an acid acceptor can be used, e.g. trialkylamines such as triethylamine and trimethylamine, pyridine, N,N-dimethyl aniline, the hydroxides, carbonates, and bicarbonates of the alkali metals and alkaline earth metals, and the alkoxides of the alkali metals, such as sodium methoxide and potassium tert-butoxide.

The reaction shown in Equation B can be carried out at a temperature between about −20° C. and 100° C., preferably between about −5° C. and 40° C. Pressure is not critical, for convenience atmospheric pressure is preferred.

The oximes of Formula III employed as reactants in Equation B can be prepared by the methods described in U.S. Pat. Nos. 3,787,470 and 3,530,220.

In the following examples all parts are by weight and temperatures are in degrees centigrade unless otherwise specified. Examples 2 and 3 are presented to illustrate use of the intermediates of Formula I for preparation of compounds with insecticidal utility.

EXAMPLE 1

N,N'-[1,2-Ethanediylbis(thio)]bis[N-methylcarbamic fluoride]

A solution of 10.2 g of ethane-1,2-disulfenyl chloride in 175 ml toluene was prepared and cooled to −35° C. under a nitrogen atmosphere. To this solution was added in one portion 9.7 g of N-methyl carbamyl fluoride. To the reaction solution was added dropwise over 0.5 hr. a solution of 12.7 g of triethylamine in 30 ml toluene, maintaining the temperature of the reaction mixture between −30° C. to −25° C. After addition was complete, the reaction mixture was stirred 0.5 hr. at −30° C. to −25° C., then allowed to warm to ambient temperature. The reaction mixture was washed with three 200-ml portions of water and dried over anhydrous magnesium sulfate. Distillation of the toluene under reduced pressure gave a brown oil which crystallized on standing. The title compound was isolated from the crude reaction product by recrystallization from 1-chlorobutane employing decolorizing charcoal. There was obtained 2.2 g of N,N'-[1,2-ethanediylbis(thio)]bis[N-methylcarbamic fluoride], m.p. 88°–90.5° C.

Calculated for $C_6H_{10}F_2N_2O_2S_2$: C, 29.50; H, 4.13; N, 11.47; S, 26.25 Found: C, 31.14; H, 4.38; N, 11.31; S, 26.34; C, 30.58; H, 4.24; N, 11.53; S. 26.01.

EXAMPLE 2

N,N'-[1,2-Ethanediylbis(thio-N-methyliminocarbonyloxy)]bis[2-(dimethylamino)-2-oxo-]ethanimidothioic Acid, Dimethyl Ester A solution of 2.44 g of N,N'-[1,2-ethanediylbis(thio)]bis[N-methylcarbamic fluoride] and 3.24 g of 2-(dimethylamino)-N-hydroxy-2-oxo-ethanimidothioic acid, methyl ester in 125 ml tetrahydrofuran was prepared. To this solution was added dropwise at ambient temperature a solution of 2.02 g of triethylamine in 10 ml tetrahydrofuran. After addition was complete, the reaction mixture was stirred 45.5 hrs. at ambient temperature. The solvent was distilled under reduced pressure to afford a yellow residue. The residue was dissolved in 100 ml methylene chloride, and the organic solution was washed with two 300-ml portions of water, a 150-ml portion of saturated sodium chloride solution, and dried over anhydrous magnesium sulfate. Distillation of the solvent under reduced pressure afforded a viscous, yellow oil which partially solidified on scratching. The gummy solid was suspended in 50-ml ethanol and the white solid was collected, washed with a few milliliters of ethanol, and dried giving 1.5 g of N,N'-[1,2-ethanediylbis(thio-N-methyliminocarbonyloxy)]bis[2-dimethylamino-2-oxo-]ethanimidothioic acid, dimethyl ester, m.p. 156°–160° C.

Calculated for $C_{16}H_{28}N_6O_6S_4$:
C, 36.35; H, 5.34; N, 15.90; S, 24.26 Found: C, 36.4; H, 5.60; N, 15.80; S, 24.2.

EXAMPLE 3

N,N'-[[1,2-Ethanediylbis[thio(methylimino)carbonyloxy]]]bis-[ethaneimidothioic acid], Dimethyl Ester A solution of 4.2 g of N-hydroxy-ethanimidothioic acid, methyl ester in a mixture of 25 ml methanol and 50 ml of toluene was prepared. To this solution was added in one portion 2.2 g of sodium methoxide, and the mixture stirred until dissolution was complete. The solution of the sodium salt of N-hydroxy-ethanimidothioic acid, methyl ester was added dropwise to a stirred suspension of 4.8 g of N,N'-[1,2-ethanediylbis(thio)]bis[N-methylcarbamic fluoride] in 100 ml of toluene, maintaining the temperature of the reaction mixture between 0° C. and 5° C. The resulting turbid reaction mixture was allowed to warm to ambient temperature, then stirred an additional hour. The solvent was distilled from the reaction mixture under reduced pressure, and the residue was dissolved in 200 ml of methylene chloride. The organic solution was washed with 150 ml water followed by 150 ml of saturated sodium chloride solution and dried over anhydrous magnesium sulfate. Distillation of the methylene chloride under reduced pressure gave a white gummy solid. The title compound was isolated by first suspending the crude reaction product in a small volume of a 1:1 mixture of 1-chlorobutane and toluene, then collecting and drying the resulting white solid. This procedure afforded 4.0 g of N,N'-[[1,2-ethanediylbis[thio(methylimino)carbonyloxy]]]bis-[ethanimidothioic acid], methyl ester, m.p. 169°–174° C.

Calculated for $C_{12}H_{22}N_4O_4S_4$: C, 34.76; H, 5.35; N, 13.51; S, 30.94; Found: C, 34.9; H, 5.59; N, 14.2; S, 29.3 C, 35.2; H, 5.76; N, 14.3; S, 29.3

I claim:
1. A compound of the formula

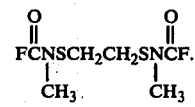

* * * * *